United States Patent [19]

Austin

[11] Patent Number: 5,596,102
[45] Date of Patent: Jan. 21, 1997

[54] BIOCIDES

[75] Inventor: Peter W. Austin, Lancashire, England

[73] Assignee: Zeneca Limited, London, England

[21] Appl. No.: 357,140

[22] Filed: Dec. 15, 1994

Related U.S. Application Data

[60] Continuation of Ser. No. 976,187, Nov. 13, 1992, abandoned, which is a division of Ser. No. 837,109, Feb. 18, 1992, Pat. No. 5,187,172, which is a continuation of Ser. No. 443,029, Dec. 1, 1989, abandoned, which is a continuation of Ser. No. 48,648, May 11, 1987, abandoned.

Foreign Application Priority Data

May 23, 1986 [GB] United Kingdom ............ 8612630

[51] Int. Cl.$^6$ .................................................. C07F 3/06
[52] U.S. Cl. ............................................ 548/101; 548/105
[58] Field of Search ................................. 548/101, 105

[56] References Cited

U.S. PATENT DOCUMENTS

| 3,448,116 | 6/1969 | McCaully et al. | 260/309.5 |
| 4,278,793 | 7/1981 | Durckheimer et al. | 544/27 |
| 4,454,216 | 6/1984 | Horii | 430/204 |

FOREIGN PATENT DOCUMENTS

| 64657 | 11/1952 | European Pat. Off. | 514/307 |
| 3510178 | 9/1986 | Germany | C07D 277/16 |
| 1104893 | 3/1968 | United Kingdom | C07D 71/00 |
| 1113634 | 5/1968 | United Kingdom | A01N 9/12 |

OTHER PUBLICATIONS

Kunig, Chem. Bur., 106:3626 (1973).
Barton, J. Chem. Soc., Perkin Trans. I, 39 (1986).
Block et al., Journal of Chemical Society, vol. 16, pp. 1061–1068 (1985).
Barton et al, Tetrahedron Letters, vol. 26, No. 48, pp. 5943–5946 (1985).
Geffken, Zeitschrift Fuer Naturforschung, vol. 38b, No. 8 (1983).
Geffken, Chemiker Zeitung, vol. 103, No. 9, pp. 299–300 (1979).
Kruger et al, Archiv Der Pharmazie, vol. 311, pp. 39–47 (1979).
Koenig et al, Chemical Abstracts, vol. 86, No. 11, Mar. 14, 1977.
Orlova et al, Chemistry of Heterocyclic Compounds, pp. 451–455 (1986).
Darby, Journal of the Chemical Society, pp. 1089–1092 (1981).
Gnichtel et al, Chemische Berichte, vol. 104, No. 5 (1971).
J. Chem. Soc. Perkin Trans. I, p. 44 (1986).
Barton J Chem Soc. Perkin Trans I pp. 44 (1986).

*Primary Examiner*—Robert Gerstl
*Attorney, Agent, or Firm*—Cushman Darby & Cushman, L.L.P.

[57] ABSTRACT

Compounds having a 5 membered, nitrogen containing ring with a thione group adjacent to a nitrogen atom substituted with an OR group have antimicrobial properties. Metal complexes or salts of these compounds also have antimicrobial properties. The compounds, or the metal complexes or salts thereof, can be used as a cutting fluid preservative, a wood preservative, in cooling water applications or as an antimicrobial agent in a paint. Some of the compounds are new. The metal complexes or salts are new.

7 Claims, No Drawings

BIOCIDES

This is a continuation of application Ser. No. 07/976,187, filed on Nov. 13, 1992, which was abandoned upon the filing hereof which is a division of Ser. No. 07/837,109, filed Feb. 18, 1992, now U.S. Pat. No. 5,187,172, which is a continuation of Ser. No. 07/443,029, filed Dec. 1, 1989, which is a continuation of Ser. No. 07/048,648, filed May 11, 1987, now abandoned.

The present invention relates to a class of compounds, some of which are new compounds, which are useful as industrial biocides.

Industrial biocides are useful to prevent industrial spoilage, in particular that caused by bacteria and fungi. Materials which can be used as industrial biocides have antimicrobial properties and particularly have antifungal or antibacterial properties, or preferably both antifungal and antibacterial properties. Such materials are useful in the preservation of paints, lattices, adhesives, leather, wood, metal working fluids and cooling water.

British Patent Specification No.1113634 discloses fungicidal compositions comprising an isothiazolothione in admixture with a solid diluent or a liquid diluent containing a surface active agent. The isothiazolothione is of the formula:

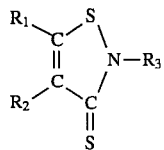

wherein $R_1$ and $R_2$ may, inter alia, together with their adjacent carbon atoms constitute a ring. Such ring systems include a cyclopentene or cyclohexene ring (compounds 8, 9 and 10) or a benzene ring (compounds 11 to 43). However, it is indicated that such compounds may isomerise to a structure containing an oxime group. The structure of compounds of this type, such as compound 41 as disclosed in GB 1113634, has been studied and it is concluded, in Il. Farmaco-Ed. Sci., Vol.23, pages 572 to 582, that in such compounds the oxime structure is more stable.

British Patent Specification No.1104893 discloses a biocidal composition in which the active ingredient is disclosed as being at least one 3-imino-1,2-dithiole derivative, such as, for example 3H-1,2-benzodithiol-3-one oxime and 4,5,6,7-tetrahydro-3H-1,2-benzo-dithiol-3-one oxime.

Cyclic compounds containing a thione group have been described in the literature but these other references do not indicate that the compounds possessed any antimicrobial activity.

U.S. Pat. No. 3,448,116 discloses, as anticonvulsants, compounds such as 1-hydroxyhydantoins and 1-hydroxythiohydantoins. J. C. S. Perkin 2, (1981), page 92ff; Chem. Ber. (1964), 97, page 216ff; Chem. Ber. (1971), 104, page 1512ff; and Arch. Pharm. (1978), 311(1), page 39ff describe cyclic compounds containing a thione group and having two nitrogen atoms in the ring adjacent to the thione group. J. C. S. Perkin 1 (1986) pages 39 to 59 discloses, inter alia, N-hydroxythiazolinthione derivatives and the preparation thereof. However, there is no suggestion that the compounds disclosed have anti-microbial properties.

We have now found that certain cyclic compounds containing a thione group and at least one adjacent amino-group have anti-microbial properties. Some compounds of this type are novel.

According to the present invention, there is provided a biocide composition which contains at least one compound of the formula:

or a metal complex or salt thereof; wherein:

A is a nitrogen or carbon atom, which may be substituted;

B and D are, independently, oxygen or sulphur or a nitrogen or carbon atom which may be substituted; or A and/or B and/or B and/or D may be part of a ring system;

R is hydrogen, a hydrocarbyl group, a substituted hydrocarbyl group, an acyl group, a substituted acyl group or a group —COOR¹; and R¹ is a hydrocarbyl group with the proviso that B and D are not both sulphur or both oxygen.

The group A, and optionally one or both of groups B and D can be a group —C(R²)₂—, a group —CR²=; a group

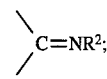

a group —NR²— or a group —N=; where R² is a hydrogen atom, a hydrocarbyl group, a substituted hydrocarbyl group or two groups R², together with the carbon atom, or carbon atoms, to which they are attached form a ring.

The groups A, B and D can form part of a further ring system but generally not more than two of the groups A, B and D form part of a further ring system. The further ring system is typically a hydrocarbon ring system containing five or six carbon atoms, for example a cyclopentene, cyclohexane, cyclohexene, cyclohexadiene or benzene ring. The further ring system, if present, typically contains one or both of the groups A and B. If only the group A forms part of a ring system, this may be a cyclohexane ring of the type

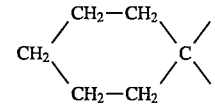

where the group A is the carbon atom with the two free valencies, which are linked to the group —NOR— and B respectively. If both A and B form part of a ring system, the further ring is then fused to the azolethione ring system; for example as in 3-hydroxy-4,5,6,7-tetrahydrobenzothiazol-2(3H)-thione.

In many of the compounds used in the biocide compositions of the present invention, the groups A, B and/or D are not part of a ring system. Thus, if A, B and/or D is a carbon atom, or substituted carbon atom, it may be, inter alia, a group —CH=, —C(CH₃)=, —C(C₂H₅)=, —C(C₆H₅)=, —C(C₆H₄Cl)=, —C(CH₃)₂ or

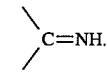

It will be appreciated that in the foregoing, the group R² is a hydrogen atom, a methyl ethyl phenyl or chlorophenyl group. Typically, $R^1$ is a hydrogen atom, a lower alkyl group, that is one containing up to five carbon atoms, an aryl group or a substituted alkyl or aryl group in which the, or each, substituent is a hydrocarbonoxy group, an acyl group, an ester (that is an acyloxy) group, a halogen atom, or a nitrile group.

It is generally preferred that the groups A and B are both optionally substituted carbon atoms and the group D is a sulphur atom. or optionally substituted nitrogen atom. The groups A and B are preferably linked through a double bond as in the group —CH═CH—. It is preferred that D is a sulphur atom.

The group R may be a hydrogen atom, an acyl group such as benzoyl or acetyl or an alkoxycarbonyl group such as an ethoxycarbonyl group. If the group R is a substituted group, it may contain a further ring system of general formula I, the two ring systems being linked through the group R, for example as in the glutaryl bis ester of the formula:

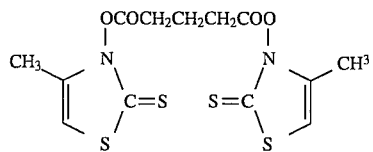

The biocide composition may contain a metal salt or complex of the compound of general formula I. The metal present in such a salt or complex may be any metal. Thus, the metal may be a transition metal, for example a metal of group VIII, IB or IIB of the Periodic Table. Such metals include iron, copper and zinc, particularly such metals in their maximum possible valency state.

All references herein to the Periodic Table are to the Periodic Table according to Mendeleeff, as set out on the inside rear cover of "General and Inorganic Chemistry" by J. R. Partington, Second Edition published by MacMillan and Co.Limited, London.

For convenience hereafter, the compounds of the general formula I, and the metal salts and complexes thereof will be referred to simply as "compound I".

A wide range of compounds I can be used in the biocide compositions of the present invention. The compounds I have anti-microbial activity against a wide range of micro-organisms including bacteria, fungi and algae.

Compounds I which can be used in the compositions of the present invention include:
3-hydroxy-4-methylthiazol-2(3H)-thione,
3-benzoyloxy-4-methylthiazol-2(3H)-thione,
3-hydroxy-4-phenylthiazol-2(3H)-thione,
3-hydroxy-4,5,6,7-tetrahydrobenzothiazol-2(3H)-thione,
3-acetoxy-4-methylthiazol-2(3H)-thione, the glutaryl bis-ester of 3-hydroxy-4-methylthiazol-2(3H)-thione,
5,5-dimethyl-1-hydroxy-4-imino-3-phenylimidazolidine-2-thione,
1-hydroxy-4-imino-3-phenyl-2-thiono-1,3-diazaspiro[4.5]decane,
1-hydroxy-5-methyl-4-phenylimidazoline-2-thione,
3-ethoxycarbonyloxy-4-methylthiazol-2(3H)-thione,
4,5-dimethyl-3-hydroxythiazol-2(3H)-thione,
4,5-dimethyl-3-acetoxythiazol-2(3H)-thione,
4-ethyl-3-hydroxy-5-methylthiazol-2(3H)-thione,
4-ethyl-3-acetoxy-5-methylthiazol-2(3H)-thione,
4-(4-chlorophenyl)-3-hydroxythiazol-2(3H)-thione,
3-hydroxy-5-methyl-4-phenylthiazol-2(3H)-thione,
3-acetoxy-4-phenylthiazol-2(3H)-thione,
and the metal complexes and salts thereof. The metal complexes and salts thereof include ferric, cupric and zinc complexes and salts such as
the zinc complex of 3-hydroxy-4-methylthiazol-2(3H)-thione,
the ferric complex of 3-hydroxy-4-methylthiazol-2(3H)-thione,
the cupric complex of 1-hydroxy-4-imino-3-phenyl-2-thion-1,3-diazaspiro[4.5]decane,
the cupric complex of 4,5-dimethyl-3-hydroxythiazol-2(3H)-thione,
the zinc complex of 4,5-dimethyl-3-hydroxythiazol-2(3H)-thione, and
the zinc complex of 4-ethyl-3-hydroxy-5-methylthiazol-2(3H)-thione.

The compositions of the present invention provide good wet state preservation making the compositions advantageous for use as a cutting fluid preservative and also in cooling water applications. Wood and leather preservation is another advantageous field of application of the compositions. The compositions of the present invention can also be incorporated into paint, as paint film fungicide and many of the compositions can be used without addition of a bactericide.

The compounds I which are present in biocide composition of the present invention are soluble in many polar solvents, although the solubility is dependent on the nature of the groups A, B, D and R. However, many of the compounds I are soluble in water, alcohols, ethers, ketones and other polar solvents or mixtures thereof.

The compositions of the present invention may consist only of the compound I. However, typically the composition comprises the compound I as a solution, suspension or emulsion in a suitable liquid medium such as water. The composition may comprise a suspension or emulsion of the compound I or a solution thereof, in a liquid medium in which the compound I is insoluble.

The composition may be incorporated into the medium to be protected using any suitable mixing technique. The composition is incorporated into the medium to be protected in an amount to provide from 0.00002 to 5% by weight of the compound I relative to the total composition, more preferably from 0.00005 to 1% by weight of compound I. It will be appreciated that the quantity of compound I required will be dependent on various factors such as the medium to be protected, the micro-organisms against which protection is desired and the extent of protection required.

If the composition is being used to preserve a solid substrate such as leather or wood, the composition may be applied directly to the substrate or may be incorporated into a coating composition such as a paint, varnish or lacquer which is then applied to the substrate. Alternatively, the solid material may be impregnated with the composition of the present invention.

The compositions of the present invention can be used for the treatment of various media to inhibit the growth of micro-organisms.

Thus, as a further aspect of the present invention there is provided a method for inhibiting the growth of micro-organisms on, or in, a medium which comprises treating the medium with a compound I as hereinbefore defined.

The compound I can be used in conditions in which micro-organisms grow and cause problems such as, for example, in aqueous environments including cooling water systems, paper mill liquors, metal working fluids, geological drilling lubricants, polymer emulsions, and emulsion paints. The compound I can also be used to impregnate solid materials such as wood or leather or can be coated onto the surfaces thereof directly or incorporated into a paint, varnish or lacquer.

The compound I may also be used to inhibit the growth of micro-organisms in agricultural and horticultural environments such as living plants, seeds etc.

The anti-microbial activity of the compositions of the present invention against both bacteria and fungi have been found to be surprisingly advantageous when compared to analogous compounds, for example derivatives disclosed in UK Patent 1113634 which are described as being isothiazoles but which may isomerise to give an isomeric oxime.

As a yet further aspect of the present invention there are provided new compounds of the formula:

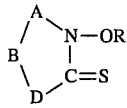
(I)

or a metal complex or salt thereof;
wherein:

A is a nitrogen or carbon atom, which may be substituted;

B and D are, independently, oxygen or sulphur or a nitrogen or carbon atom which may be substituted; or A and/or B, and/or B and/or D may be part of a ring system;

R is hydrogen, a hydrocarbyl group, a substituted hydrocarbyl group, an acyl group, a substituted acyl group or a group —COOR$^1$; and R$^1$ is a hydrocarbyl group with the proviso that B and D are not both sulphur or both oxygen, and with the further provisos that if the compound is other than a metal complex or salt thereof, when D is —NH— and R is H or COCH$_3$, A and B are not both groups C(CH$_3$)$_2$;

when D is —NH— and R is H, the group A is other than =C(CH$_3$)— or =C(C$_6$H$_5$)— when the group B is =C(C$_6$H$_5$)— or =C(CH$_3$)— respectively;

when D is —N(C$_6$H$_5$)— and R is H, the group A is other than —C(CH$_3$)$_2$— when B is

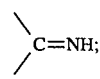

and when D is —S— and R is H or COC$_{15}$H$_{31}$, the group A is other than =C(CH$_3$)— or =C(C$_6$H$_5$)— when B is =CH—.

As a particular feature of the present invention there is provided a metal complex or salt of a compound of formula I subject only to the proviso that B and D are not both sulphur or both oxygen.

Metal complexes or salts in accordance with this aspect of the present invention include ferric, cupric and zinc complexes or salts.

New compounds of formula I include
3-benzoyloxy-4-methylthiazol-2(3H)-thione,
3-hydroxy-4,5,6,7-tetrahydrobenzothiazol-2(3H)-thione,
3-acetoxy-4-methylthiazol-2(3H)-thione,
the glutaryl bis-ester of 3-hydroxy-4-methylthiazol-2(3H)-thione,
3-ethoxycarbonyloxy-4-methylthiazol-2(3H)-thione,
4,5-dimethyl-3-hydroxythiazol-2(3H)-thione,
4,5-dimethyl-3-acetoxythiazol-2(3H)-thione,
4-ethyl-3-hydroxy-5-methylthiazol-2(3H)-thione,
4-ethyl-3-acetoxy-5-methylthiazol-2(3H)-thione,
4-(4-chlorophenyl)-3-hydroxythiazol-2(3H)-thione,
3-hydroxy-5-methyl-4-phenylthiazol-2(3H)-thione,
3-acetoxy-4-phenylthiazol-2(3H)-thione,
and the metal complexes or salts thereof.

The compounds of the present invention may be prepared by known procedures for example as described in J. C. S. Perkin 1, (1986) pages 39 to 59.

A convenient method of preparing compounds in which the group R is hydrogen is by the cyclisation under basic conditions of the corresonding oximine-dithiocarbonate. Derivatives in which R is other than hydrogen are conveniently prepared by known methods from the corresponding compound in which R is hydrogen, for example by reaction with an acid chloride or acid anhydride or with an ester of chloroformic acid. The metal derivatives are conveniently prepared by the reaction of the compound, particularly one in which the group R is hydrogen, with a salt of the metal, for example a metal sulphate or acetate.

The preparation of the compound, or metal complex or salt, may be effected in any suitable solvent such as, for example, water, a lower alkanol, an aqueous lower alkanol, a ketone such as acetone, N,N-dimethylformamide, N-methylpyrrolidone, glyme, diglyme and cellosolve.

The reaction is preferably effected at a relatively low temperature, for example, not more than 80° C. and especially not more than 30° C., which may be ambient temperature or below for example 15° C. If the reaction is effected at a temperature above ambient temperature, it is conveniently effected in acetone under reflux, that is at a temperature between 55° and 60° C.

The desired compound can be isolated and purified using any suitable technique. Thus, the compound may be recrystallised from a suitable solvent or solvent mixture, for example from a mixture of methylene chloride and a low boiling petroleum ether fraction. Alternatively, the compound may be purified by a chromatographic technique, for example by flash chromatography.

Further aspects of the present invention are described in the following illustrative examples.

In the following examples, the products obtained were subjected to microbiostatic evaluation. The microbiological testing was effected, under sterile conditions throughout, as follows:

Preparation of Inoculum

Bacteria

The bacterial inoculum consisted of 24 hour cultures of the organisms grown in Oxoid Nutrient Broth, subcultured daily and incubated at 37° C.

Fungi

Spore suspensions of each of the test fungi were prepared as follows. To 250 cm$^3$ conical flasks containing well sporulating cultures of the organisms, growing on Oxoid Malt Extract agar, a number of sterile 3 mm glass beads and approximately 50 cm$^3$ of a sterile solution of 0.01% v/v of polyoxyethylene (20) sorbitan mono-oleate (available from Imperial Chemical Industries PLC as Tween 80) (Tween is a Registered Trade Mark) in water were added. Each flask was swirled so that the beads removed the spores and the resulting suspension was poured into a sterile 100 g medical flat bottle containing approximately 50 cm$^3$ of the sterile 0.01% v/v solution of Tween 80. The suspension could be stored for up to four weeks at 4° C.

In the microbiological testing, the products were tested for anti-microbial activity against bacteria and/or fungi. The bacteria used were one or more of *Escherichia coli, Staphylococcus aureus,* and *Pseudomonas aeruginosa.* The fungi used were one or more of *Aspergillus niger, Aureobasidum pullulans, Cladosporium sphaerospermum, Aspergillus versicolor,* and *Chaetomium globosum.*

These test organisms will be referred to hereafter as EC, SA, PA, AN, AP, CS, AV and CG respectively.

Microbiostatic evaluation

Method A 0.3 g of the product to be tested was dissolved in 3.0 cm$^3$ of N,N-dimethylformamide to give a 10% w/v solution.

For each of the products being tested, five bottles containing 50 cm$^3$ of Oxoid Malt agar and five bottles containing 50 cm$^3$ of Oxide Nutrient agar were heated by steam to melt the contents. The bottles were cooled to 50° C. and a sufficient quantity of the solution of the product was added to give a concentration of the product in the agar of 1 ppm, 5 ppm, 25 ppm, 125 ppm or 625 ppm. The lower concentrations of product were obtained by diluting the initial 10% w/v solution to 1% w/v or 1000 ppm and adding the diluted solution to the melted agar. From each bottle treated as described, two petri dish plates were poured and allowed to set overnight.

The test organisms were surface inoculated onto the test plates by means of a multi-point inoculator.

The test plates obtained from malt agar were inoculated with fungi and the plates were incubated at 25° C. for five days.

The test plates obtained from nutrient agar were inoculated with bacteria and the plates were incubated for 24 hours at 37° C.

At the end of the incubation period, the plates were assessed visually for growth of the micro-organisms. The concentration of the product which inhibited the growth of a particular micro-organism was recorded.

Method B 100 mg of the product to be tested was dissolved in 2 cm$^3$ of N,N-dimethylformamide and the solution obtained diluted with a further quantity of N,N-dimethylformamide to give a product concentration of 2500 ppm.

To bottles containing 50 cm$^3$ of Czapek Dox agar containing 0.5% v/v peptone at 50° C. was added a quantity of the product solution to give a concentration of 500 ppm or 25 ppm of the product. In some tests, concentrations of 250 ppm, 50 ppm and/or 5 ppm of the product were also examined. From each bottle, two petri dish plates were poured and allowed to set overnight.

The test organisms were surface inoculated onto the test plates by means of a multi-point inoculator. Each test plate was inoculated with both bacteria and fungi. The plates were incubated for four days at 25° C.

At the end of the incubation period, the plates were assessed visually for growth of the micro-organisms. The concentration of the product which inhibited the growth of a particular micro-organism was recorded.

In all of the following examples parts are by weight with the exception of solvents where parts are by volume.

EXAMPLE 1

A compound of formula I was prepared in which the group A is —C(CH$_3$)=, the group B is —CH=, the group D is —S— and R is hydrogen.

0.885 parts of 0-ethyl-5-(2-oximinopropyl)dithiocarbonate were added to 30 parts of methylene chloride. The solution was stirred at 0°–5° C. and 10 parts of aqueous 2N potassium hydroxide solution were added dropwise. 25 parts of methylene chloride and 25 parts of water were then added, the aqueous layer was separated and carefully acidified by the cautious addition of aqueous 2N hydrochloric acid. The aqueous fraction was then extracted with ethyl acetate, the extract was dried using anhydrous magnesium sulphate and evaporated to dryness. The residue was recrystallised from a mixture of ethyl acetate and petroleum ether (b.pt. 60°–80° C.) to give 3-hydroxy-4-methylthiazol-2(3H)-thione, m.pt. 95°–96.5° C. By analysis the composition was found to be C 32.8% wt; H 3.3% wt; and N 9.5% wt. C$_4$H$_5$NOS$_2$ requires C 32.6% wt; H 3.4% wt; and N 9.5% wt.

EXAMPLE 2

A zinc salt of the product of Example 1 was prepared.

0.98 parts of 3-hydroxy-4-methylthiazol-2(3H)-thione were stirred in 50 parts of water and aqueous 2N sodium hydroxide was added till a clear solution was achieved (pH 8). 0.96 parts of zinc sulphate heptahydrate were added and the reaction mixture was stirred for one hour at room temperature. The product was collected by filtration, washed with cold water and dried. The product was dissolved by boiling in 100 parts by volume of chloroform and the resulting solution was screened. 100 parts by volume of petroleum ether (b.pt. 60°–80° C.) were added to the clear filtrate to precipitate the zinc complex which was collected by filtration after cooling and was dried. The product had a melting point of 268°–270° C. By analysis the composition was found to be C 26.8% wt; H 2.2% wt; N 7.7% wt; S 35.2% wt and Zn 17.7% wt. (C$_4$H$_4$NOS$_2$)$_2$Zn requires C 26.9% wt; H 2.2% wt; N 7.8% wt; S 25.8% wt and Zn 18.3% wt.

EXAMPLE 3

The benzoyl derivative of the product of Example 1 was prepared, that is R is COC$_6$H$_5$, A, B and D are as in Example 1.

0.735 parts of 3-hydroxy-4-methylthiazol-2(3H)-thione were stirred in 50 parts of water and 0.84 parts of sodium hydrogen carbonate. The solution was screened and 0.9 parts of benzoyl chloride were added. The reaction mixture was stirred overnight at room temperature. A precipitate was formed which was separated by filtration, washed with cold water and recrystallised from ethanol to give 3-benzoyloxy-4-methylthiazol-2(3H)-thione, m.pt. 100°–102° C. By analysis the composition was found to be C 52.4% wt; H 3.6% wt; N 5.6% wt and S 25% wt. C$_{11}$H$_9$NO$_2$S$_2$ requires C 52.6% wt; H 3.6% wt; N 5.6% wt and S 25.5% wt.

EXAMPLE 4

For comparison purposes, the following compounds were prepared.

Compound A

One gramme of 4,5,6,7-tetrahydro-3H-1,2-benzodithiol-3-thione was mixed with 2.2 g of anhydrous sodium acetate and 2 g of hydroxylamine hydrochloride in 22 cm$^3$ of methylated spirits. The mixture was stirred under reflux for four hours and allowed to cool to ambients temperature overnight. The mixture was heated to boiling, screened and evaporated to dryness. The residue was washed with two 10 cm$^3$ portions of methylated spirits at 65° C. The combined washings were evaporated to dryness and the solid was redissolved in methanol. A small proportion of product of melting point 114° to 116° C. crystallised. The liquid was separated, water was added and a precipitate was formed. The precipitate was filtered off and dried to give a solid of melting point 146°–148° C. The infra red spectrum of this material contained a sharp peak at 1600 cm$^{-1}$ characteristic of the oxime group (C=NOH), indicating that the product was 4,5,6,7-tetrahydro-3H-1,2-benzodithiol-3-one oxime rather than the isomeric thione compound which is compound 10 in GB 1113634.

Compound B 2.5g of 3H-1,2-benzodithiol-3-one were mixed with 5 g of anhydrous sodium acetate and 5 g of hydroxylamine hydrochloride in 100 cm$^3$ of methylated spirits. The mixture was stirred, heated to reflux and maintained under reflux for ten minutes. The mixture was cooled, water was added forming a precipitate, the mixture was filtered and the solid was washed with water at 10°–15° C. The solid was dissolved in methylated spirits at 65° C. the solution was screened whilst still hot and the solid crystallised and dried. The solid obtained had a melting point of 212°–214° C., which corresponds closely with the reported melting point (208° C.) of 3H-1,2-benzodithiol-3-one oxime, indicating the oxime had been obtained rather than the isomeric thione compound which is compound 41 of GB 1113634.

The compounds of Examples 1 to 3 and Compounds A and B obtained as described, were evaluated against a range of bacteria and fungi using Method A as previously described. Control for the test organisms was obtained at the levels set out in the Table.

TABLE

| Compound | Micro-organisms (concentrations in ppm) | | | | | | | |
|---|---|---|---|---|---|---|---|---|
| (a) | EC | PA | SA | AN | AP | CS | AV | CG |
| 1 | 25 | 625 | 125 | 1 | 1 | 1 | 1 | 1 |
| 2 | 25 | 125 | 25 | 5 | 5 | 5 | 5 | 5 |
| 3 | 125 | NA | 125 | 25 | 25 | 25 | 25 | 25 |
| A | NA | NA | NA | 125 | 125 | 125 | 125 | 125 |
| B | NA | NA | NA | NA | 625 | NA | NA | 625 |

Notes to Table
(a) 1, 2 and 3 are the products of Examples 1, 2 and 3 respectively, A and B are Compounds A and B respectively. NA means control not achieved at the highest level tested (625). Levels lower than 1 ppm were not tested. The number represents the lowest level (in ppm) at which control was achieved.

EXAMPLE 5

A ferric salt of the product of Example 1 was prepared.

0.5 parts of the compound obtained as described in Example 1 were dissolved in one part of ethanol. Four parts of a cold saturated aqueous solution of ferrous sulphate were added dropwise, with stirring, to the alcohol solution. The mixture was stirred at ambient temperature for 15 minutes and the solid product formed was obtained by filtration. The precipitate was washed successively with water and ethanol, boiled with chloroform, refiltered and dried. By analysis the product was found to be a 3:1 complex indicating oxidation of the iron had occurred to the trivalent state. The product had a melting point of 220° C., with decomposition. By analysis the composition was found to be C 29.5% wt; H 2.5% wt; N 8.3% wt and Fe 9.7% wt. $(C_4H_4NOS_2)_3Fe$ requires C 29.1% wt; H 2.4% wt; N 8.5% wt and Fe 11.3% wt.

In microbiostatic evaluation using Method A, the compound provided control of the test organisms as follows:

| AP | 25 ppm |
| CS | 25 ppm |
| AV | 25 ppm |
| CG | 25 ppm. |

EXAMPLE 6

A compound of formula I was prepared in which the group A is —C(C$_6$H$_5$)=, the group B is —CH=, the group D is —S— and R is hydrogen.

7.96 parts of phenacyl bromide and 8.34 parts of hydroxylamine hydrochloride were stirred overnight at ambient temperature in 75 parts of methanol and 25 parts of water. A further 200 parts of water were then added and a solid product separated which was filtered off, dried and recrystallised from petroleum ether (b.pt. 60°–80° C.) to yield 3.5 parts of the oxime (m.pt. 88°–89° C.).

3.89 parts of the oxime, 2.9 parts of potassium ethyl xanthate and 22 parts of acetone were stirred overnight at ambient temperature. The reaction mixture was evaporated to dryness and the residue was dissolved in water. The resulting aqueous solution was extracted with three portions of diethyl ether (each portion was 50 parts by volume). The diethyl ether extract was dried using anhydrous magnesium sulphate and the ether was evaporated off to give the xanthate (3.9 parts) as a yellow oil. The oil was dissolved in 15 parts of ether and the solution was added to a mixture of 2.3 g of powder zinc chloride in 30 parts of diethyl ether which was being stirred at 0°–5° C. The mixture was stirred overnight and allowed to warm up to ambient temperature. The ethereal layer was separated by decantation and the residual syrup was digested with a further 30 parts of ether.

The residue was then stirred vigorously with a mixture of 15 parts of methylene chloride, 15 parts of water and 15 parts of 36% aqueous hydrochloric acid, filtered off, and recrystallised from propan-1-ol to yield 0.14 parts of 3-hydroxy-4-phenylthiazol-2(3H)-thione of melting point 149°–151° C.

In microbiostatic evaluation using Method A, the compound provided control of the test organisms as follows:

| EC | 125 ppm |
| AN | 125 ppm |
| AP | 125 ppm |
| CS | 25 ppm |
| AV | 25 ppm |
| CG | 25 ppm. |

EXAMPLE 7

A compound of formula I was prepared in which the group D is —S—, R is hydrogen and A and B together form a cyclohexene ring.

6.63 parts of 2-chlorocyclohexanone were used in a procedure essentially as described in Example 6 to form, as intermediates, the oxime (m.pt. 62°–73° C.) and the xanthate (m.pt. 67°–72° C.). The final product was 3-hydroxy-4,5,6,7-tetrahydrobenzothiazol-2(3H)-thione having a melting point of 111.5° to 114° C.

By analysis the composition was found to be C 44.5% wt; H 5.0% wt; N 7.6% wt and S 34.1% wt. $C_7H_9ONS_2$ requires C 44.9% wt; H 4.8% wt; N 7.5% wt and S 34.2% wt.

In microbiostatic evaluation using Method A, the compound provided control of the test organisms as follows:

| | |
|---|---|
| EC | 25 ppm |
| CA | 25 ppm |
| AN | 125 ppm |
| AP | 125 ppm |
| CS | 125 ppm |
| AV | 125 ppm |
| CG | 125 ppm. |

EXAMPLE 8

The acetoxy derivative of the product of Example 1 was prepared, that is R is $COCH_3$, A, B and D are as in Example 1.

0.74 parts of 3-hydroxy-4-methylthiazol-2(3H)-thione, 0.84 parts of sodium bicarbonate and 30 parts of water were stirred at 0°–5° C. while 0.52 parts of acetic anhydride were added dropwise and the reaction mixture was stirred at 0°–5° C. for a further hour. A precipitate was formed which was separated by filtration and recrystallised from aqueous methanol. 0.33 parts of 3-acetoxy-4-methylthiazol-2(3H)-thione, of melting point 100°–101° C., was obtained.

By analysis the composition was found to be C 38% wt; H 3.7% wt; N 7.3% wt and S 34.0% wt. $C_6H_7O_2NS_2$ requires C 38.1% wt; H 3.7% wt; N 7.4% wt and S 33.9% wt.

In microbiostatic evaluation using Method A, the compound provided control of the test organisms as follows:

| | |
|---|---|
| EC | 25 ppm |
| SA | 125 ppm |
| AN | 25 ppm |
| AP | 5 ppm |
| CS | 5 ppm |
| AV | 5 ppm |
| CG | 5 ppm. |

EXAMPLE 9

A bis-ester of the product of Example 1 and glutaric acid was prepared.

The procedure of Example 8 was repeated using 0.42 parts of glutaryl chloride rather than acetic anhydride. The glutaryl bis-ester, of melting point 104.5°–106.5° C., was obtained.

By analysis the composition was found to be C 39.8% wt; H 3.8% wt; N 6.7% wt and S 32.5% wt. $C_{13}H_{14}N_2O_4S_4$ requires C 40.0% wt; H 3.6% wt; N 7.2% wt and S 32.8% wt.

In microbiostatic evaluation using Method A, the compound provided control of the test organisms as follows:

| | |
|---|---|
| EC | 25 ppm |
| SA | 25 ppm |
| AN | 25 ppm |
| AP | 5 ppm |
| CS | 5 ppm |
| AV | 5 ppm |
| CG | 5 ppm. |

EXAMPLE 10

A compound of formula I was prepared in which the group A is —$C(CH_3)_2$—, the group B is —C(NH)—, the group D is —$N(C_6H_5)$— and R is hydrogen.

11.6 parts of acetone, 15 parts of hydroxylamine hydrochloride and 66 parts of water were stirred vigorously at 0°–5° C. while a solution of 11 parts of potassium cyanide in 33 parts of water was added over a period of 0.5 hours. The solution formed was stored at ambient temperature for two days and then neutralised to pH 6–7 with sodium acetate. The neutral solution was stored for a further five days and then extracted with chloroform. The chloroform extract was dried and evaporated to dryness. The residue was recrystallised twice from petroleum ether (b.pt. 60°–80° C.) to yield 1.4 parts of 1-hydroxyamino-1-methylpropionitrile of melting point 98°–105° C.

The nitrile product was dissolved in 28 parts of toluene being stirred at ambient temperature and 1.9 parts of phenyl isothiocyanate were added. The reaction mixture was stirred overnight, evaporated to dryness and purified by flash chromatography on Kieselgel 60 (a silica gel available from Merck GmbH of Darmstadt, Germany). Elution was effected using petroleum ether (b.pt. 60°–80° C.) with increasing proportions of chloroform. 0.18 parts of 5,5-dimethyl-1-hydroxy-4-imino-3-Phenylimidazolidine-2-thione were obtained as an amorphous solid.

By analysis the composition was found to be C 56.3% wt; H 5.4% wt; N 16.5% wt and S 13.0% wt. $C_{11}H_{13}N_3OS$ requires C 56.1% wt; H 5.5% wt; N 17.9% wt and S 13.6% wt.

In microbiostatic evaluation using Method A, the compound provided control of the test organisms as follows:

| | |
|---|---|
| AN | 25 ppm |
| AP | 25 ppm |
| CS | 25 ppm |
| AV | 25 ppm |
| CG | 25 ppm. |

EXAMPLE 11

A compound of formula I, and the cupric complex thereof, were prepared in which the group A is a spirocyclohexyl group

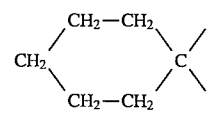

and B, D and R are as in Example 10.

The procedure of Example 10 was repeated using cyclohexanone. The product obtained was converted to the 2:1 cupric complex by reaction with cupric sulphate using the procedure of Example 2.

By analysis the composition was found to be N 12.9% wt and Cu 8.9% wt. $(C_{14}H_{16}N_3OS)_2Cu3H_2O$ requires N 12.6% wt and Cu 9.4% wt.

In microbiostatic evaluation using Method A, the compound provided control of the test organisms as follows:

| | |
|---|---|
| AN | 25 ppm |
| AP | 25 ppm |
| CS | 25 ppm |
| AV | 25 ppm |
| CG | 25 ppm. |

EXAMPLE 12

A compound of formula I was prepared in which the group A is —C(CH$_3$)=, the group B is —C(C$_6$H$_5$)=, the group D is —NH— and R is hydrogen.

15.1 parts of C-phenylglycine, 100 parts of acetic anhydride and 100 parts of pyridine were heated at 90° C. until all evolution of carbon dioxide had ceased. The reaction mixture was evaporated to give an oil. 300 parts of toluene were added and this mixture was evaporated to give a solid residue.

The solid residue was stirred under reflux with 200 parts of aqueous 5N hydrochloric acid. The resulting solution was screened and evaporated to dryness. The solid residue was recrystallised from ethanol to yield 11.65 parts of alpha-acetylbenzylamine hydrochloride, of melting point 204.5°–206.5° C.

4.65 parts of this hydrochloride and 3.5 parts of hydroxylamine hydrochloride were stirred in 25 parts of water. The mixture was stirred whilst being boiled and 8.25 parts of sodium acetate dissolved in 20 parts of water were added. The reaction mixture was stirred overnight whilst being allowed to cool to room temperature. A further 1.75 parts of hydroxylamine hydrochloride and 4.15 parts of sodium acetate dissolved in 10 parts of water were added, the reaction mixture was stirred for four hours at 50° C. and the reaction mixture was then cooled to 0°–5° C. A precipitate was formed which was separated by filtration and dissolved in 40 parts of water containing one part of sodium carbonate. This solution was extracted with chloroform and the chloroform was evaporated to give 1.99 parts of an oxime of melting point 73°–74.5° C.

1.64 parts of the oxime and 2.8 parts of triethylamine were dissolved in 33 parts of tetrahydrofuran (solution A). 0.8 parts of thiophosgene were dissolved in 33 parts of tetrahydrofuran (solution B). Solutions A and B were added simultaneously over a period of one hour to 133 parts of tetrahydrofuran which were being stirred at −65° C. The reaction mixture was allowed to warmup to 0° C. overnight and was then screened and evaporated to dryness. The solid was recrystallised from ethanol to give 0.27 parts of 1-hydroxy-5-methyl-4-phenylimidazoline-2-thione having a melting point of 202° C.

By analysis the compound was found to contain 12.9% wt of nitrogen. C$_{10}$H$_{10}$N$_2$OS requires 13.6% wt of nitrogen.

In microbiostatic evaluation using Method B, the compound provided control of the test organisms as follows:

| EC | 500 ppm |
|----|---------|
| SA | 500 ppm |
| AN | 500 ppm |
| AP | 25 ppm |
| CS | 500 ppm |
| AV | 25 ppm |
| CG | 25 ppm. |

EXAMPLE 13

The ethoxycarbonyl derivative of the product of Example 1 was prepared, that is R is C$_2$H$_5$OCO, A, B and D are as in Example 1.

0.98 parts of the product of Example 1 were dissolved in parts of toluene and treated with 0.6 parts of triethylamine and 0.72 parts of ethyl chloroformate at ambient temperature. Further portions of triethylamine and ethyl chloroformate were added at intervals until no more of the starting material was present, as indicated by thin layer chromatography. The reaction mixture was screened, evaporated to dryness and the product purified by flash chromatography (as in Example 10) to obtain 3-ethoxycarbonyloxy-4-methylthiazol-2(3H)-thione as a semi-solid gum.

By analysis the composition was found to be C 37.7% wt; H 4.3% wt; N 6.4% wt and S 31.3% wt. C$_7$H$_9$NO$_3$S$_2$ requires C 38.4% wt; H 4.1% wt; N 6.4% wt and S 29.2% wt.

In microbiostatic evaluation using Method B, the compound provided control of the test organisms as follows:

| EC | 25 ppm |
|----|--------|
| PA | 500 ppm |
| SA | 50 ppm |
| AN | 25 ppm |
| AP | 5 ppm |
| CS | 25 ppm |
| AV | 25 ppm |
| CG | 5 ppm. |

EXAMPLE 14

A compound of formula I was prepared in which the group A is —C(CH$_3$)=, the group B is —C(CH$_3$)=, the group D is —S— and R is hydrogen.

53.25 parts of 3-chloro-2-butanone were added dropwise over a period of 15 minutes to a rapidly stirred slurry of 52.12 parts of hydroxylamine hydrochloride in 50 parts of water at ambient temperature. The mixture was stirred for one hour at ambient temperature and was then cooled to 0°–5° C. The mixture at 0°–5° C. was neutralised with sodium carbonate solution and stirred for a further hour whilst warming up to ambient temperature. The solution was contacted with diethyl ether and the ether extract was dried and evaporated to dryness to give 51 parts of the oxime as a pale yellow oil (Proton magnetic resonance using CDCl$_3$ as solvent and tetramethylsilane as internal reference showed a doublet peak at a delta value of 1.6 ppm, a singlet peak at a delta value of 1.9 ppm, a quadruplet peak at a delta value of 4.6 ppm and a broad singlet peak at a delta value of 9 ppm).

12.15 parts of the oxime were reacted with potassium ethyl xanthate using the procedure as generally described in Example 6 to obtain a solid xanthate having a melting point of 62°–64° C.

The xanthate was cyclised using dilute potassium hydroxide, the procedure being generally as described in Example 1. 4,5-dimethyl-3-hydroxythiazol-2(3H)-thione was isolated as a white crystalline solid.

By analysis the compound was found to contain 8.3% wt of nitrogen. C$_5$H$_7$NOS$_2$ requires 8.7% wt of nitrogen. The proton magnetic resonance spectrum, obtained as described previously, showed singlets at delta values of 2.18 and 2.2 ppm.

In microbiostatic evaluation using Method B, the compound provided control of the test organisms as follows:

| EC | 25 ppm |
|----|--------|
| SA | 500 ppm |
| AN | 25 ppm |

| | |
|---|---|
| AP | 25 ppm |
| CS | 5 ppm |
| AV | 5 ppm |
| CG | 5 ppm. |

EXAMPLE 15

The acetoxy derivative of the product of Example 14 was prepared, that is R is $COCH_3$, A, B and D are as in Example 14.

The procedure of Example 8 was repeated with the exception that 0.8 parts of the product of Example 14 were used. 4,5-dimethyl-3-acetoxythiazol-2(3H)-thione was obtained as a white solid.

By analysis the composition was found to be C 41.3% wt; H 4.5% wt; N 6.9% wt and S 32.1% wt. $C_7H_9NO_2S_2$ requires C 41.3% wt; H 4.4% wt; N 6.9% wt and S 31.5% wt.

In microbiostatic evaluation using Method B, the compound provided control of the test organisms as follows:

| | |
|---|---|
| EC | 25 ppm |
| AN | 25 ppm |
| AP | 25 ppm |
| AV | 25 ppm |
| CG | 25 ppm. |

EXAMPLE 16

The cupric complex of the compound of Example 14 was prepared.

0.99 parts of cupric acetate dissolved in 50 parts of methanol were added with stirring to a stirred solution of 1.61 parts of 4,5-dimethyl-3-hydroxythiazol-2(3H)-thione in 50 parts of methanol at ambient temperature. The mixture was stirred at ambient temperature for four hours, a green precipitate, of the 2:1 cupric complex, was isolated by filtration and then washed with water at 10°–15° C. and dried. The solid had a melting point of 250°–252° C.

By analysis the composition was .found to be C 31.0% wt; H 3.1% wt; N 7.1% wt and Cu 15.7% wt. $(C_5H_7NOS_2)_2Cu$ requires C 31.3% wt; H 3.1% wt; N 7.3% wt and Cu 16.6% wt.

In microbiostatic evaluation using Method B, the compound provided control of the test organisms as follows:

| | |
|---|---|
| AP | 25 ppm |
| AV | 25 ppm |
| CG | 25 ppm. |

EXAMPLE 17

The zinc complex of the compound of Example 14 was prepared.

1.2 parts of 4,5-dimethyl-3-hydroxythiazol-2(3H)-thione were reacted with zinc acetate in methanol using the procedure of Example 16. The 2:1 zinc complex was obtained as a white solid of melting point 235°–238° C.

By analysis the composition was found to be C 31.3% wt; H 3.1% wt; N 7.1% wt and Zn 16.6% wt. $(C_5H_6NOS_2)_2Zn$ requires C 31.2% wt; H 3.1% wt; N 7.3% wt and Zn 16.9% wt.

In microbiostatic evaluation using Method B, the compound provided control of the test organisms as follows:

| | |
|---|---|
| EC | 25 ppm |
| SA | 500 ppm |
| AN | 25 ppm |
| AP | 25 ppm |
| CS | 25 ppm |
| Av | 25 ppm |
| CG | 25 ppm. |

EXAMPLE 18

A compound of formula I was prepared in which the group A is $—C(C_2H_5)=$, B is $—C(CH_3)=$, D is —S— and R is hydrogen.

33 parts of 2-bromopentan-3-one were treated as described in Example 14 to obtain the oxime and the xanthate as intermediates and finally to obtain, as the final product, 4-ethyl-3-hydroxy-5-methylthiazol-2(3H)-thione as a solid of melting point 87°–89° C.

By analysis the composition was found to be C 41.3% wt; H 5.6% wt; N 8.1% wt and S 36.2% wt. $C_6H_9NOS_2$ requires C 41.1% wt; H 5.1% wt; N 8.0% wt and S 36.6% wt.

In microbiostatic evaluation using Method A, the compound provided control of the test organisms as follows:

| | |
|---|---|
| EC | 25 ppm |
| AN | 125 ppm |
| AP | 25 ppm |
| CS | 125 ppm |
| AV | 25 ppm |
| CG | 5 ppm. |

EXAMPLE 19

The acetoxy derivative of the product of Example 18 was prepared, that is R is $COCH_3$, A, B and D are as in Example 18.

The procedure of Example 8 was repeated with the exception that 0.82 parts of the product of Example 18 was used.

By analysis the composition was found to be C 44% wt; H 5.2% wt; N 6.5% wt and S 29.5% wt. $C_8H_{11}NO_2S_2$ requires C 44.2% wt; H 5.1% wt; N 6.5% wt and S 29.5% wt.

In microbiostatic evaluation using Method B, the compound provided control of the test organisms as follows:

| | |
|---|---|
| EC | 25 ppm |
| AN | 500 ppm |
| AP | 500 ppm |
| CS | 500 ppm |
| AV | 500 ppm |
| ·CG | 500 ppm. |

EXAMPLE 20

The zinc complex of the compound of Example 18 was prepared.

The procedure was as described in Example 17 with the exception that 1.35 parts of the compound of Example 18 were used. The solid zinc complex had a melting point of 204°–210° C.

By analysis the composition was found to be C 35% wt; H 4.0% wt; N 6.8% wt; S 30.4% wt and Zn 15.6% wt. $(C_6H_8NOS_2)_2Zn$ requires C 34.9% wt; H 3.9% wt; N 6.8% wt; S 31% wt and Zn 15.3% wt.

In microbiostatic evaluation using Method B, the compound provided control of the test organisms as follows:

| | |
|---|---|
| EC | 25 ppm |
| AN | 500 ppm |
| AP | 500 ppm |
| CS | 500 ppm |
| AV | 500 ppm |
| CG | 25 ppm. |

EXAMPLE 21

A compound of formula I was prepared in which the group A is $—C(C_6H_4Cl)=$, B is $—CH=$, D is $—S—$ and R is hydrogen.

The procedure of Example 6 was repeated with the exception that 4-chlorophenacylbromide was used rather than phenacylbromide. The final product was 4-(4-chlorophenyl)-3-hydroxythiazol-(2(3H)-thione, which was obtained as a white solid.

By analysis the composition was found to be N 5.2% wt and S 25.6% wt. $C_9H_6ClNOS_2$ requires N 5.7% wt and S 26.3% wt.

In microbiostatic evaluation using Method A, the compound provided control of the test organisms as follows:

| | |
|---|---|
| EC | 25 ppm |
| SA | 125 ppm |
| AN | 125 ppm |
| AP | 125 ppm |
| CS | 125 ppm |
| AV | 125 ppm |
| CG | 125 ppm. |

EXAMPLE 22

A compound of formula I was prepared in which the group A is $—C(C_6H_5)=$, B is $—C(CH_3)=$, D is $—S—$ and R is hydrogen.

The procedure of Example 6 was repeated with the exception that w-chloro-w-methylacetophenone was used rather than phenacylbromide to obtain 3-hydroxy-5-methyl-4-phenylthiazol-2(3H)-thione. The proton magnetic resonance spectrum, obtained as described in Example 14, showed singlets at delta values of 2.05 ppm and 7.3 ppm. In microbiostatic evaluation using Method A, the compound provided control of the test organisms as follows:

| | |
|---|---|
| EC | 125 ppm |
| SA | 125 ppm |
| AN | 125 ppm |
| AP | 5 ppm |
| cs | 25 ppm |
| AV | 25 ppm |
| CG | 5 ppm. |

EXAMPLE 23

The acetoxy derivative of the product of Example 6 was prepared, that is R is $COCH_3$, A, B and D are as in Example 6.

The procedure of Example 8 was repeated with the exception that one part of the product of Example 6 was used. 3-acetoxy-4-phenylthiazol-2(3H)-thione was obtained as a white solid. The proton magnetic resonance spectrum, obtained as described in Example 14, showed singlets at delta values of 2.1 ppm, 6.45 ppm and 7.35 ppm.

By analysis the compound was found to contain 5.6% wt of nitrogen. $C_{11}H_9NO_2S_2$ requires 5.6% wt. of nitrogen.

I claim:

1. A metal complex of a compound of formula I

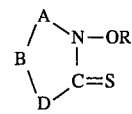

wherein the metal is copper or a metal of Group VIII or IIB of the Periodic Table, A and B are independently selected from $—C(R^2)_2—$, $—CR^2=$ or $>C=NR^2$;

D is $—NR^2—$ or sulphur

R is hydrogen; and $R^2$ is hydrogen, $C_{1-6}$ hydrocarbyl, $C_{1-6}$ hydrocarbyl substituted by halogen or two groups $R^2$ together with the carbon atom or carbon atoms to which they are attached form a 5- or 6-membered hydrocarbon ring system.

2. The metal complex of claim 1 wherein A and B are $—CR^2=$ and D is sulphur.

3. The metal complex of claim 1 wherein the metal is iron, copper or zinc.

4. The metal complex of claim 1 of:
3-hydroxy-4-methylthiazol-2(3H)-thione,
3-hydroxy-4-phenylthiazol-2(3H)-thione,
3-hydroxy-4,5,6,7-tetrahydrobenzothiazol-2(3H)-thione,
5,5-dimethyl-1-hydroxy-4-imimo-3-phenylimidazolidine-2-thione,
1-hydroxy-4-imino-3-phenyl-2-thiono-1,3-diazaspiro[4,5]decane,
4,5-dimethyl-3-hydroxythiazol-2(3H)-thione,
4-ethyl-3-hydroxy-5-methylthiazol-2(3H)-thione,
4-(4-chlorophenyl)-3-hydroxythiazol-2(3H)-thione,
3-hydroxy-5-methyl-4-phenylthiazol-2(3H)-thione,
1-hydroxy-5-methyl-4-phenyl imidazoline-2-thione, or
3-hydroxy-5-methyl-4-phenylthiazol-2(3H)-thione.

5. The zinc complexes of claim 1 of:
3-hydroxy-4-methylthiazole-2(3H)-thione,
4,5-dimethyl-3-hydroxythiazole-2(3H)-thione and
4-ethyl-3-hydroxy-5-methylthiazole-2(3H)-thione.

6. A metal complex as claimed in claim 1 wherein $R^2$ is selected from the group hydrogen, methyl, ethyl, phenyl or chlorophenyl.

7. A metal complex as claimed in claim 1 wherein the groups A and B are linked through a double bond.

* * * * *